US012589005B2

(12) United States Patent
   Peyman et al.

(10) Patent No.: US 12,589,005 B2
(45) Date of Patent: Mar. 31, 2026

(54) INTERBODY SPINAL CAGE

(71) Applicants: Nazmi Peyman, Richmond, VA (US);
   Edmond Zahedi, Burnaby (CA);
   Steven Fiore, Midlothian, VA (US)

(72) Inventors: Nazmi Peyman, Richmond, VA (US);
   Edmond Zahedi, Burnaby (CA);
   Steven Fiore, Midlothian, VA (US)

( * ) Notice: Subject to any disclaimer, the term of this
   patent is extended or adjusted under 35
   U.S.C. 154(b) by 0 days.

(21) Appl. No.: 19/053,017

(22) Filed: Feb. 13, 2025

(65) Prior Publication Data

US 2025/0186218 A1      Jun. 12, 2025

Related U.S. Application Data

(62) Division of application No. 17/709,361, filed on Mar.
   30, 2022, now Pat. No. 12,251,319.

(60) Provisional application No. 63/168,126, filed on Mar.
   30, 2021.

(51) Int. Cl.
   *A61F 2/44*          (2006.01)
(52) U.S. Cl.
   CPC ............ *A61F 2/4455* (2013.01); *A61F 2/442*
   (2013.01); *A61F 2220/0025* (2013.01)

(58) Field of Classification Search
   CPC . A61F 2/442; A61F 2/4455; A61F 2220/0025
   See application file for complete search history.

(56) References Cited

U.S. PATENT DOCUMENTS 5,827,328 A  *  10/1998  Buttermann ............ A61F 2/442
                                             623/17.13

* cited by examiner

*Primary Examiner* — Sameh R Boles
(74) *Attorney, Agent, or Firm* — Barry Choobin; Patent
360

(57) ABSTRACT

An interbody spinal cage when implanted can be manipu-
lated non-invasively to change dimensions conforming to
contours of adjacent vertebral bones. The interbody spinal
cage includes a flexible shell that encases multiple variable-
length rods. Each of the multiple variable-length rods
includes telescoping tubes and an actuator for increasing and
decreasing the length of the telescoping tubes. Each of the
variable-length rods includes a retention member to limit
movements of the telescoping tubes, wherein the retention
member can be engaged and disengaged. Both the retention
member and the actuator can be operated from outside the
body in which the interbody spinal cage is implanted.

5 Claims, 25 Drawing Sheets

40

600

40

800

840

820

830

810

850

1100

1105

1110

1130

1120

1510    1520

INTERBODY SPINAL CAGE

CROSS-REFERENCE TO RELATED APPLICATIONS

This application is a divisional of a U.S. patent application Ser. No. 17/709,361, filed on Mar. 30, 2022, which claims priority from the U.S. provisional patent application Ser. No. 63/168,126, filed on Mar. 30, 2021, both of which are incorporated herein by reference in its entirety.

FILED OF INVENTION

The present invention relates to an interbody spinal cage, and more particularly, the present invention relates to an interbody spinal cage that can be adapted to its environment by changing its dimensions.

BACKGROUND

A certain number of factors, including genetics, age, lifestyle, and trauma may lead to the degeneration of the intervertebral discs, necessitating spinal fusion surgery and in some cases inter-vertebral disc replacement. The most common method for spinal fusion surgery is the use of an interbody spinal cage. In this method, the degenerated intervertebral disk is completely removed and after polishing the surfaces of the adjacent vertebrae, the interbody spinal cage is inserted between the adjacent vertebrae to fill the void created by the removal of the intervertebral disk. Generally, the physical dimensions of this cage are determined by a medical expert based on radiological images and other tests taken before surgery. The dimensions can be further adjusted to the actual intervertebral spacing during surgery. The cage acts as a spacer between the two vertebral bones allowing the bones to grow through it.

One major problem with this approach is that despite proper surgical techniques, the surfaces of the bones may remain uneven even after the polishing, therefore the pressure contact at the bone-cage interface may not be properly distributed. In some cases, there may be little or no contact pressure at all, leading to poor bone growth. However, according to Wolf's law, suitable contact pressure is required to allow suitable bone growth. This uneven distribution of the load can also be partially attributed to the fact that during surgery, the patient is under general anesthesia, therefore the spinal position is dictated by this particular state where muscles are completely relaxed, while the patient is lying on the operating bed.

In most cases, the dimensions of the implanted cage may need to be readjusted once the patient has resumed normal activities. However, the process of readjusting the interbody spinal cage post-surgery is complex and often requires another surgery. Another surgery comes with added complications and discomfort to the patient. Moreover, the patient would again be under general anesthesia, therefore the confounding factors leading to a less-than-optimal load distribution would still be present, necessitating another cycle of surgery.

Thus, a need is appreciated for a system and method that is devoid of the aforementioned drawbacks of interbody spinal cages and the method of implanting the interbody spinal cages.

SUMMARY OF THE PRESENT INVENTION

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a novel interbody spinal cage and a system that allows for post-operative and non-invasive manipulation of the dimensions of the interbody spinal cage to conform to the adjacent vertebral bones.

It is another object of the present invention that surgery or surgeries to readjust the interbody spinal cage is/are avoided.

It is still another object of the present invention that the adjustments can be made without subjecting the patient to anesthesia.

It is yet another object of the present invention that the cost of re-surgery can be avoided.

It is a further object of the present invention that the interbody spinal cage promotes even growth of the adjacent vertebral bones.

It is still a further object of the present invention that the readjustments can be made as and when necessary.

It is an additional object of the present invention that the interbody spinal cage can be used to optimize the fusion of the interbody spinal cage to the bones.

In one aspect, disclosed is an interbody spinal cage comprising a plurality of variable length rods, wherein each of the plurality of variable length rods comprises an inner tube that has a proximal end and a distal end; an outer tube that has a proximal end and a distal end, wherein the distal end of the inner tube is slidably received within the outer tube through the proximal end of the outer tube, wherein the inner tube is configured to telescopically slide within the outer tube; a retention member configured to limit movement of the inner tube relative to the outer tube; a retention member micro-actuator configured to selectively engage and disengage the retention member; and a tube actuator coupled to the distal end of the inner tube and configured to at least push the inner tube relative to the outer tube; and one or more shells, wherein each shell of the one or more shells encases one or more variable length rods of the plurality of variable length rods, wherein the each shell of the one or more shells is extensible in at least one direction, wherein the extension of the each shell of the one or more shells is caused by the respective one or more variable length rods.

In one implementation, each shell of one or more shells is flexible.

In one implementation, one or more variable-length rods are arranged radially in each shell of one or more shells.

In one implementation, one or more variable-length rods are arranged randomly in each shell of one or more shells.

In one implementation, the retention member is a permanent magnet pin, the outer tube, and the inner tube have corresponding holes spaced at regular intervals along a length of the outer tube, wherein the permanent magnet pin is configured to engage by being received within one of the holes of the outer tube and within one of the holes of the inner tube, wherein engaging of the permanent magnet pin limits movement of the inner tube relative to the outer tube.

In one implementation, the retention member micro-actuator is an electromagnet configured to generate a magnetic field causing engagement and disengaging of the permanent magnet pin, wherein the electromagnet is configured to be energized from an external source of energy.

In one implementation, the tube actuator is a spring configured to provide passive actuation.

In one implementation, the tube actuator is configured to be operated from an external controller for pushing and pulling the inner tube for active actuation.

In one aspect, disclosed is an interbody spinal cage comprising a plurality of support elements, wherein each of the plurality of support elements comprises a shell encasing one or more variable length rods, each of the one or more variable length rods comprises: an inner tube that has a proximal end and a distal end, an outer tube that has a proximal end and a distal end, wherein the distal end of the inner tube is slidably received within the outer tube through the proximal end of the outer tube, wherein the inner tube is configured to telescopically slide within the outer tube, a retention member configured to limit movement of the inner tube relative to the outer tube, a retention member micro-actuator configured to selectively engage and disengage the retention member, and a tube actuator coupled to the distal end of the inner tube and configured to at least push the inner tube relative to the outer tube, wherein the shell is extensible in at least one direction, wherein the extension of the each shell of the one or more shells is caused by the one or more variable length rods; and a plurality of linking members configured to assemble the plurality of support elements into a frame.

In one implementation, the shell comprises an upper rigid section, a lower rigid section, and a middle extensible section, wherein the middle extensible section extends between the upper rigid section and the lower rigid section.

In one implementation, the frame comprises a rigid top, a rigid bottom, and an extensible mesh wall that perpendicularly extends between the rigid top and the rigid bottom.

In one implementation, the frame further comprises a joint configured to divide the frame into two sections, wherein the two sections are capable of being flexed at the joint.

In one implementation, each of the one or more variable length rods comprises a pressure sensor configured to measure a force on the inner tube.

In one aspect, disclosed is a method for correcting spinal disorders, the method comprising the steps of providing an interbody spinal cage comprising a plurality of variable length rods, wherein each of the plurality of variable length rods comprises an inner tube that has a proximal end and a distal end, an outer tube that has a proximal end and a distal end, wherein the distal end of the inner tube is slidably received within the outer tube through the proximal end of the outer tube, wherein the inner tube is configured to telescopically slide within the outer tube, a retention member configured to limit movement of the inner tube relative to the outer tube, a retention member micro-actuator configured to selectively engage and disengage the retention member, and a tube actuator coupled to the distal end of the inner tube and configured to at least push the inner tube relative to the outer tube, and one or more shells, wherein each shell of the one or more shells encases one or more variable length rods of the plurality of variable length rods, wherein the each shell of the one or more shells is extensible in at least one direction, wherein the extension of the each shell of the one or more shells is caused by the respective one or more variable length rods; and implanting the interbody spinal cage.

BRIEF DESCRIPTION OF THE DRAWINGS

The accompanying figures, which are incorporated herein, form part of the specification and illustrate embodi-ments of the present invention. Together with the description, the figures further explain the principles of the present invention and enable a person skilled in the relevant arts to make and use the invention.

FIG. 10A is a horizontal distribution of variable-length rods, FIG. 10B is a star distribution of the variable-length rods, and FIG. 10C shows a random distribution of the variable length rods, according to an exemplary embodiment of the present invention.

Figures 1A, 1B:
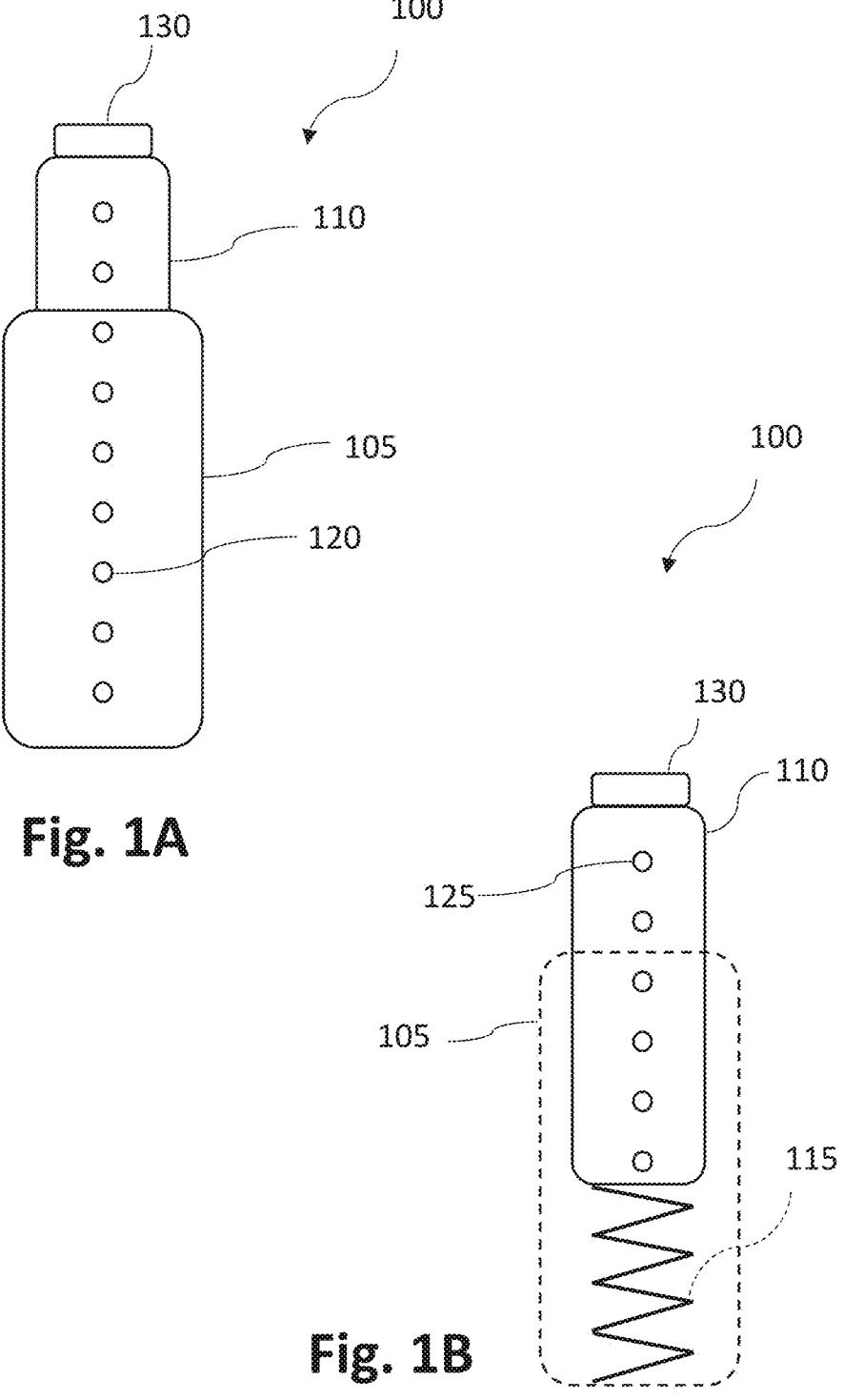
FIG. 1A depicts a variable-length rod of the disclosed interbody spinal cage having telescoping tubes, pressure sensors, and embedded data transmission circuits, according to an exemplary embodiment of the present invention.
FIG. 1B shows spring, according to an exemplary embodiment of the present invention.

The drawings referred to in this description should be understood as not being drawn to scale except if specifically indicated.

DESCRIPTION OF EMBODIMENTS

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, the reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is to describe particular embodiments only and is not intended to be limiting to embodiments of the invention. As used herein, the singular forms "a", "an", and "the" are intended to include the plural forms as well, unless the context indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely to illustrate the general principles of the invention since the scope of the invention will be best defined by the allowed claims of any resulting patent.

Furthermore, in the following description of embodiments, numerous specific details are outlined to provide a thorough understanding of the present technology. However, the present technology may come together in the form of a complete assembly without these specific details. In some instances, well-known methods, procedures, devices, and circuits have not been described in detail so as not to unnecessarily obscure aspects of the present embodiments.

Disclosed is an interbody spinal cage, the dimensions of which can be changed so that the interbody spinal cage can closely fit between the vertebral bones and no-contact/no-load areas/zones can be avoided between the bone cage interface, thus promoting uniform bone growth. The dimensions of the implanted interbody spinal cage can be manipulated noninvasively, which can be of particular advantage, thus avoiding the complications and cost of subsequent surgeries.

Referring to FIG. 1A which shows an exemplary embodiment of a variable length rod 100 that can be increased and decreased in height. The variable-length rod 100 can include two telescopic tubes i.e., an outer tube 105 and an inner tube 110. Each of the outer tube and the inner tube has a proximal end and a distal end. The distal end of the inner tube can be slidably inserted into the outer tube through the proximal end of the outer tube. Referring to FIG. 1B, shows the variable-length rod 100 in which the outer tube 105 is hidden to show inside the telescoping tube. The distal end of the inner tube 110 can be coupled to an actuating member 115 that pushes the inner tube relative to the outer tube. The actuating member can be a spring that can provide passive actuation. The stiffness of the spring can be chosen/adjusted before surgery to accommodate the forces that will be encountered by the variable-length rod. The vertebral bones adjacent to the disclosed interbody spinal cage can be repositioned relative to each other, wherein the repositioning of the bones results in compression of certain springs and decompression of other springs of the interbody spinal cage. FIG. 1B shows a recoil spring as a passive actuation element that can exert a force on the inner tube so that the inner tube stays extended. In one implementation, the stiffness of the spring can be adjusted such that it corresponds to the pressure required to keep the rod fully extended when the disclosed interbody spinal cage is implanted between the two vertebrae. Each of the outer and inner tubes can have corresponding holes at spaced intervals along the length of the variable-length rod. FIG. 1 shows the holes 120 in the outer tube and holes 125 in the inner tube. A retention pin can be inserted through a hole in the outer tube and into a hole in the inner tube to restrict the movement of the inner tube relative to the outer tube. However, it is understood that the holes and pins can be replaced by any other retention element known to a skilled person for immobilizing telescoping tubes, and any such retention element is within the scope of the present invention. The retention pin can be engaged and disengaged as and when required to allow adjusting the position of the inner tube relative to the outer tube, and so adjusting the length of the variable-length rod.

The variable-length rod can further include suitable pressure sensors 130 that can sense an external pressure or force on the proximal end of the inner tube. The pressure sensor 130 can be coupled to a circuitry embedded within the variable-length rod, wherein the circuitry can send the pressure value to an external device. The pressure sensor and the embedded circuitry can be powered by an implanted battery. Alternatively, the pressure sensor and the embedded circuitry can be powered by an external power supply, such as a wireless power supply. For example, when a reading is required, the external source of energy can power the pressure sensor and the embedded circuitry so that it transmits back the measured pressure value. In certain implementations, the circuitry can include a passive circuit that alters an external energy field, and the amount of such alteration is reflective of the measured pressure value. In this case, the external field source provides the field necessary for the sensor to create the alteration hence transmitting back the measured pressure value. As such, the design of the sensor passive circuitry is simplified because there is no need for an internal energy element.

Figures 2A, 2B:
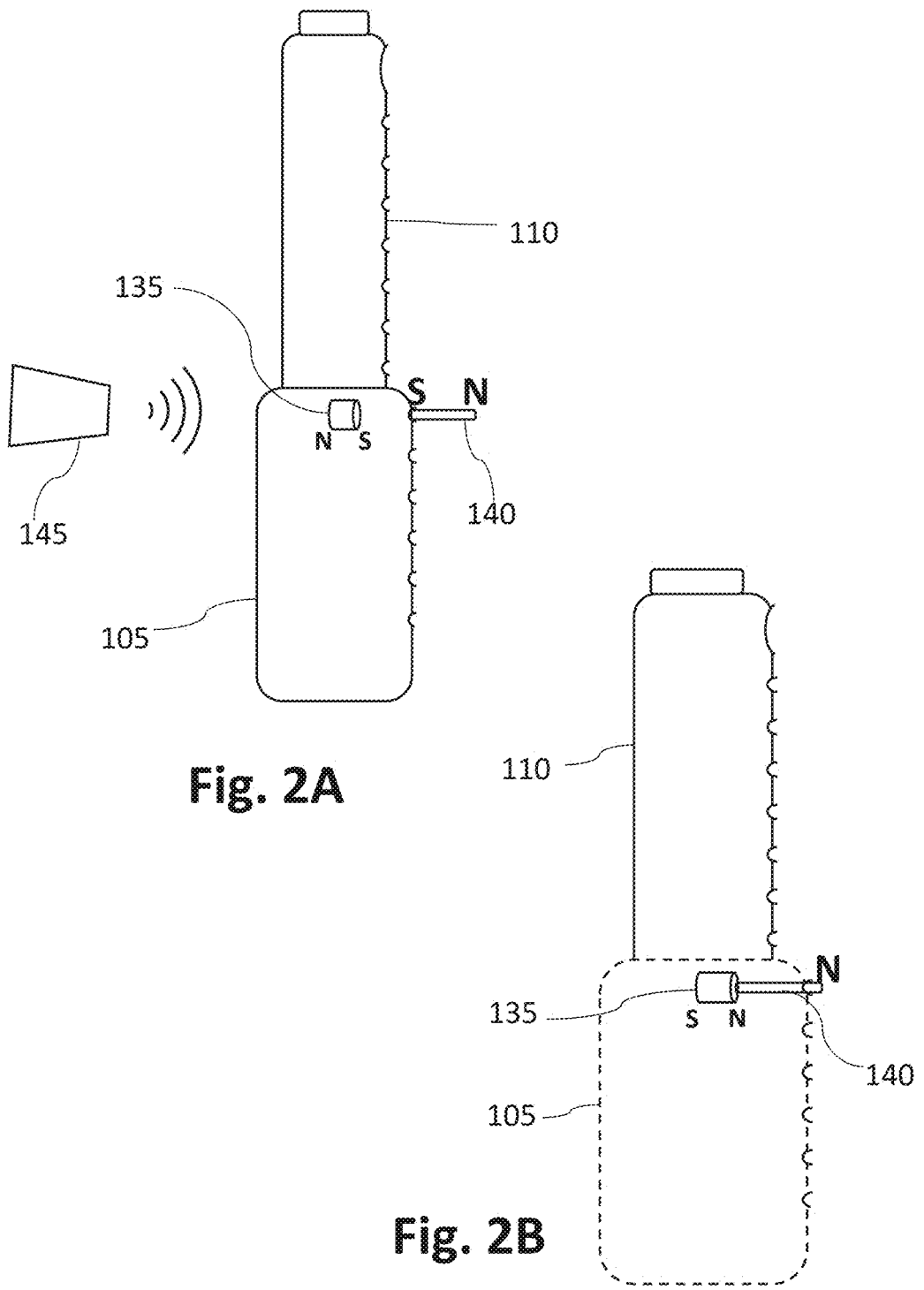
FIG. 2A is a schematic diagram to depict disengaging of the retention pin, according to an exemplary embodiment of the present invention.
FIG. 2B is a schematic diagram showing engaging of the retention pin to limit the movement of the telescoping tubes, according to an exemplary embodiment of the present invention.

The readings can be used to determine the optimum length of the variable resistance rod. For example, the patient can make certain predefined body postures to achieve the optimum length of the rod. During this maneuver, the spring continues to exert a force to keep the inner tube fully extended. The retention pins can be engaged and disengaged from an external source. Referring to FIGS. 2A & 2B show magnet-based retention members, wherein the pin can be a permanent magnet. The variable-length rod 100 can have an electromagnetic pin microactuator 135. An external source of energy 145 can power the electromagnetic pin microactuator 135. The polarities of the electromagnetic pin microactuator can be changed by the external source of energy 145 to engage or disengage the magnetic pin 140. For example, the like poles can repel the magnetic pin resulting in disengaging of the magnetic pin. Oppositely, the, unlike poles, can pull the magnetic pin resulting in the engaging of the magnetic pin. It is understood, however, that any other mechanism known to a skilled person for engaging and disengaging a retention member non-invasively is within the scope of the present invention.

As shown in FIG. 2A, once the magnetic retention pin is disengaged, the inner and outer telescopic tubes can move freely with respect to each other, under the control of the medical expert. Once the optimum length of the variable-length rod can be achieved, as determined by the pressure sensors, the magnetic retention pin can be engaged to immobile the telescoping tubes at the optimum length. While FIG. 2A shows a single magnetic retention pin, the reader of the application will appreciate that more than one magnetic retention pin can be used without departing from the scope of the present invention.

The disclosed interbody spinal cage can include one or more of such variable length rods, such that to allow for the shape of the interbody spinal cage to follow as closely as possible to the contour of the bone(s) to which it is exposed. Under the external source of energy 145, the locking pins of all the variable-length rods can be disengaged, then by changing the positions and/or orientations of the bones adjacent to the implanted interbody spinal cage, the intervertebral distances are modified and as a result, the variable-length rods may elongate if there is room for the spring to expand or compress if the externally applied force (by the new positions of the bones) overcomes the force exerted by the spring, depending on the desired outcome/effect. The readings from the pressure sensors can be analyzed to determine the amount of pressure on the variable-length rods, and suitable action can be taken to achieve the optimum pressure. the polarities of the electromagnetic pin microactuator 135 can be reversed by the external source of energy 145, as shown in FIG. 2B to cause the engaging of the magnetic pins 140.

Figure 3:
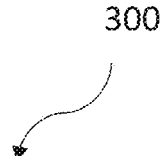
FIG. 3 shows a flexible outer shell of the interbody spinal cage, according to an exemplary embodiment of the present invention.
Figure 3:
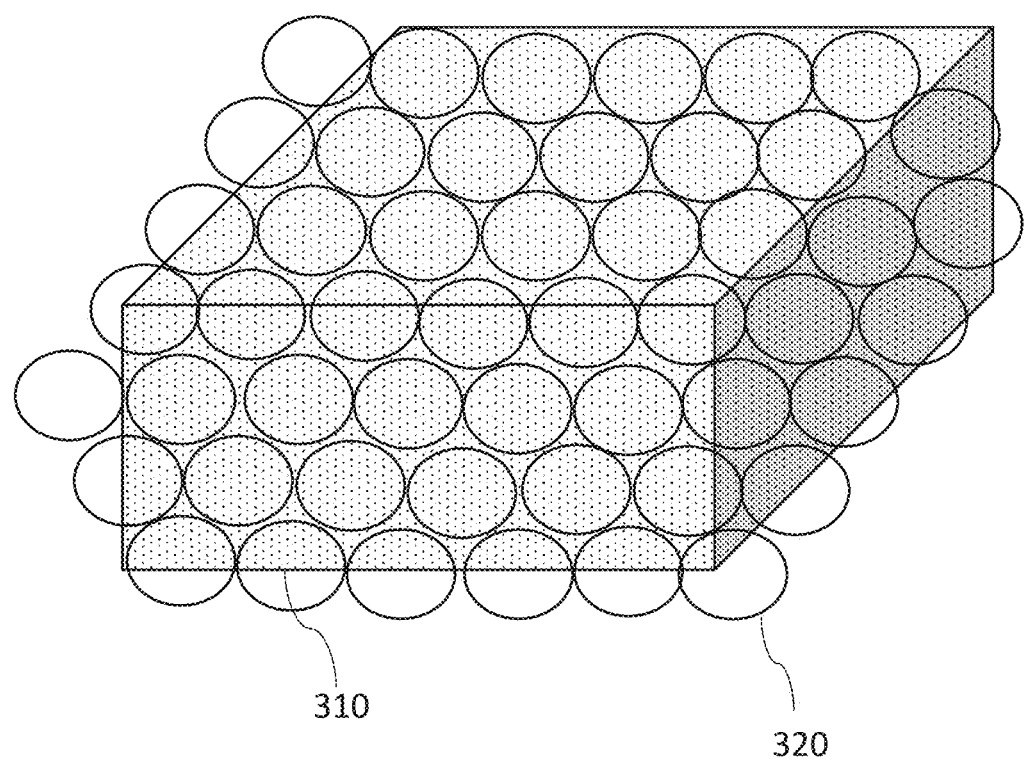
Figure 4:
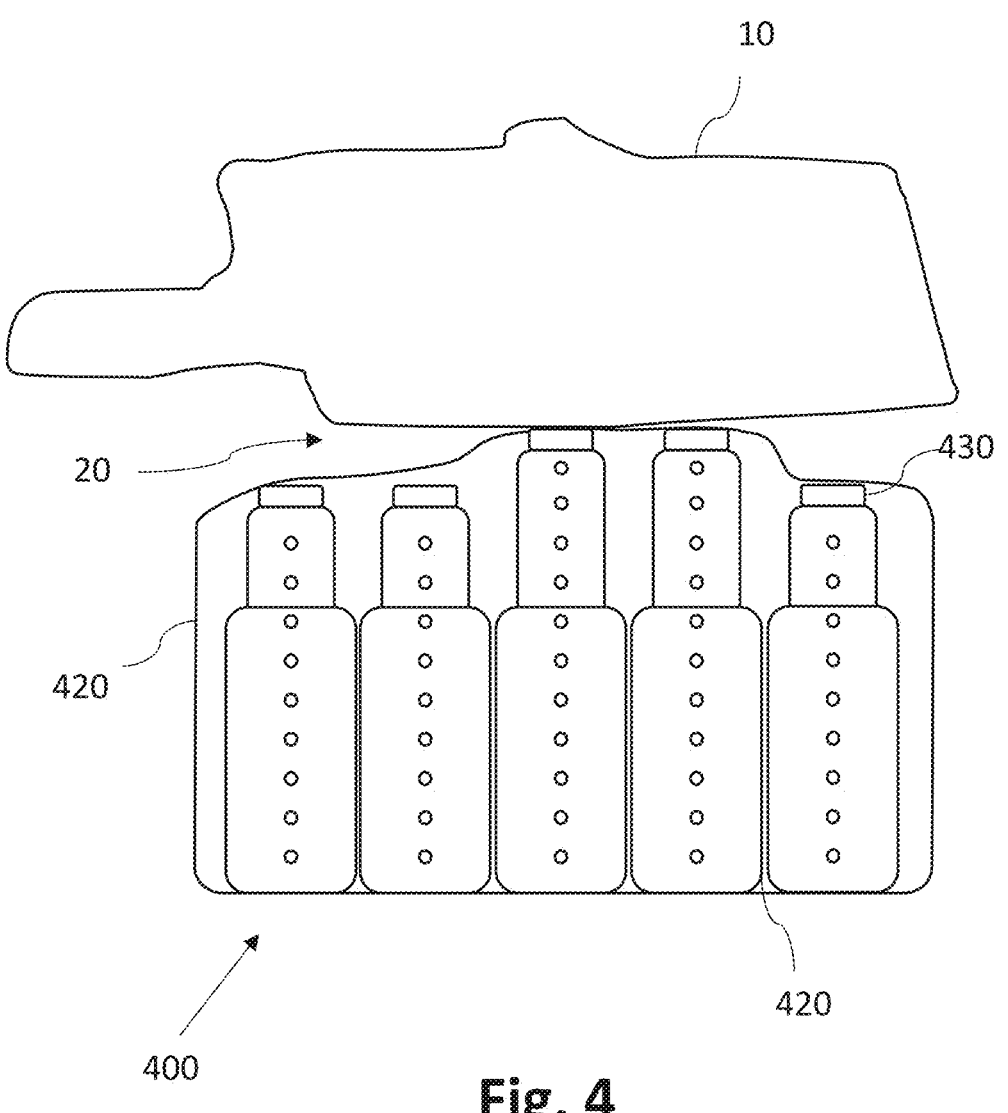
FIG. 4 shows an interface between a vertebral bone and an implanted interbody spinal cage, further showing no contact zones between the vertebral bone and the interbody spinal cage, according to an exemplary embodiment of the present invention.
Figure 5:
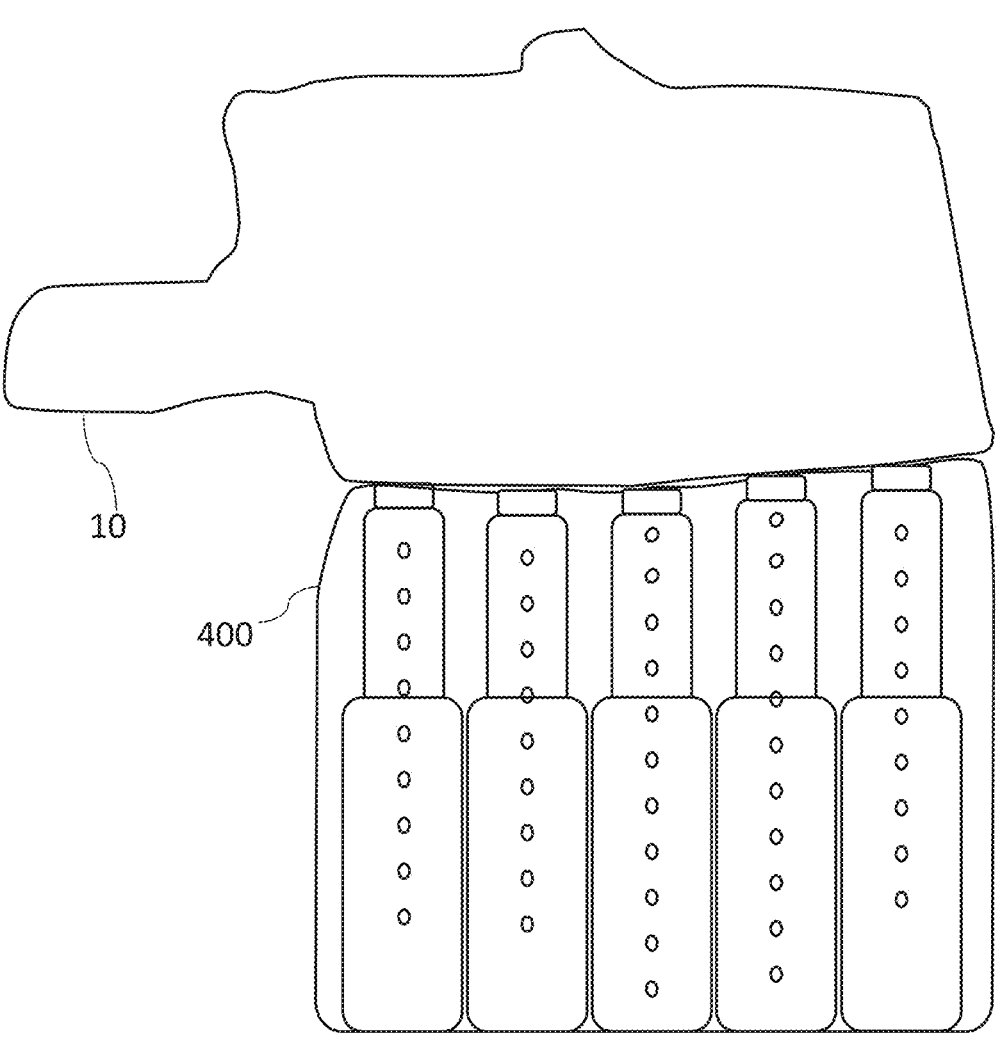
FIG. 5 shows the vertebral bone as in FIG. 4 and the interbody spinal cage adjusted to overcome the non-contact zone to allow for uniform bone growth, according to an exemplary embodiment of the present invention.

Referring to FIG. 3 which illustrates the architecture of the disclosed interbody spinal cage 300. The interbody spinal cage can include an extensible outer shell 310 made from a series of interwoven rings 320, structured in such a way that the shell or a portion of the shell can expand and contract. For example, the extension of variable length rods can extend the shell and the contraction of the variable length rods results in contraction of the shell or the respective shell portion. The variable-length rods can extend and contract non-uniformly. Moreover, some of the variable-length rods can extend while others may contract. Thus, when the lengths of the variable-length rods are adjusted, the outer shells get deformed by following the contour dictated by the variable-length rods. Referring to FIGS. 4 and 5, wherein FIG. 4 shows the disclosed interbody spinal cage 400 implanted against a bone 10. FIG. 4 shows the interbody spinal cage having multiple variable-length rods 410. The variable-length rods in the interbody spinal cage are of non-uniform lengths and shell 420 is deformed according to the arrangement of the variable-length rods 410. Also, there are non-contact zones 20 or areas at the interface of shell 420 and bone 10. The pressure sensors 430 are also shown that can determine the pressure exerted by the bone 10 on the inner tube of the variable-length rods 410. It is to be understood that the pressure sensors are shown on the proximal end of the inner tube are for illustration only, the position of the pressure sensors can be varied without departing from the scope of the present invention. FIG. 5 shows the bone-cage interface after optimization has been carried out and no-contact zones are no longer present. The disclosed interbody spinal cage 400 adapts to the contours of the bones for uniform pressure on the bones and uniform bone growth. Using the capability of rod-length adjustment, it is possible to extend or retract chosen rods so that they reach their optimum length.

Figure 6:
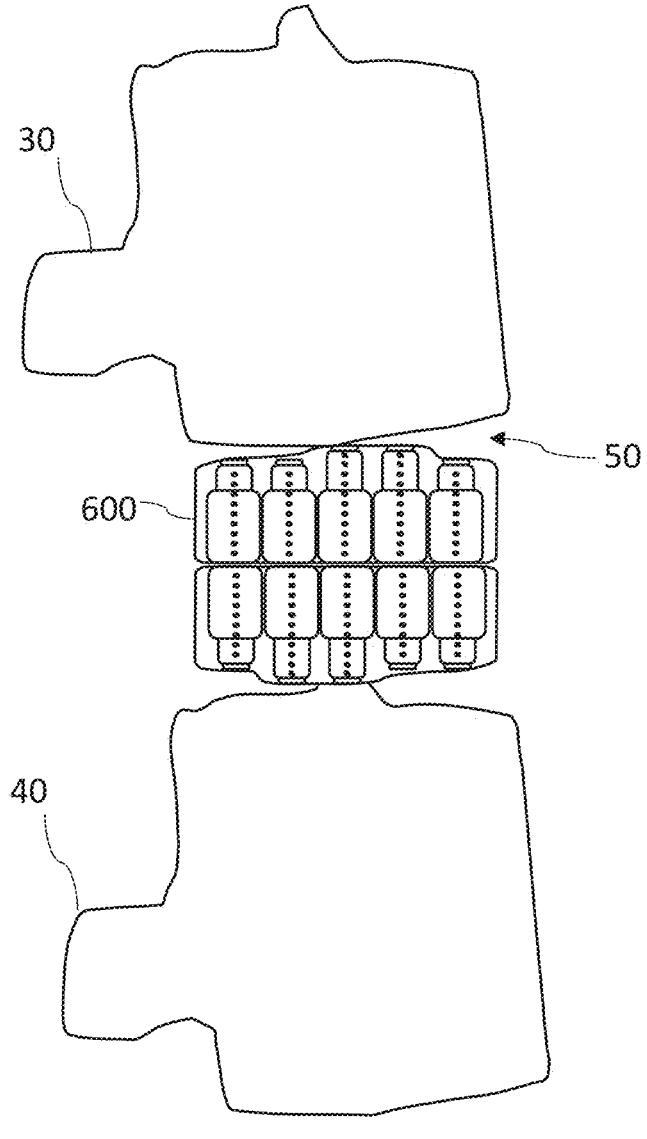
FIG. 6 shows the placement of the interbody spinal cage between two vertebral bones, further showing the no contact zones between the vertebral bones and the interbody spinal cage, according to an exemplary embodiment of the present invention.
Figure 7:
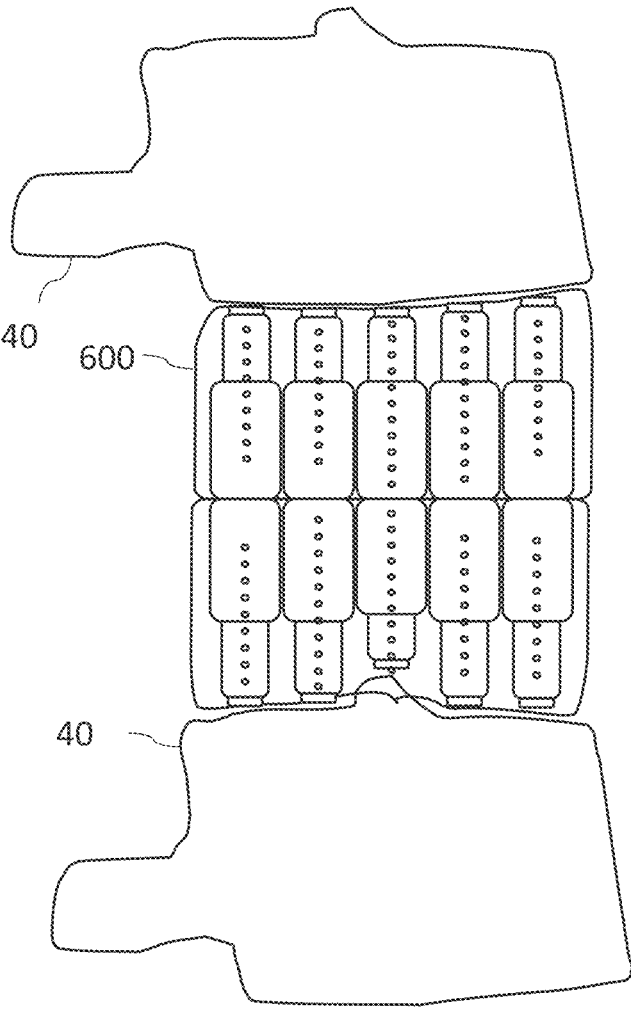
FIG. 7 shows the image of FIG. 6 in which the interbody spinal cage has been readjusted to overcome the non-contact zone, according to an exemplary embodiment of the present invention.

FIG. 6 shows the interbody spinal cage 600 sandwiched between two vertebral bones 40 whereas the interbody spinal cage 600 is in need of readjustment by changing the lengths of the variable-length rods to fill in the non-contact zones 50. The shape of the interbody spinal cage 600 can be adapted by changing the length of variable length rods. Such zones of low or no contact may appear on any of the surfaces and prevent uniform bone growth. The variable-length rods can be extended and retracted so that they reach their optimum length. FIG. 7 shows the interbody spinal cage 600 that has been adjusted by changing the lengths of the variable-length rods to fill in the gaps and provide maximum contact between the interbody spinal cage and the adjacent bones. The shape of the interbody spinal cage shown in FIG. 7 has been adapted by changing the lengths of multiple variable-length rods encased within a shell of the interbody spinal cage, and the non-contact zones 50 are no longer present in FIG. 7.

Figure 8:
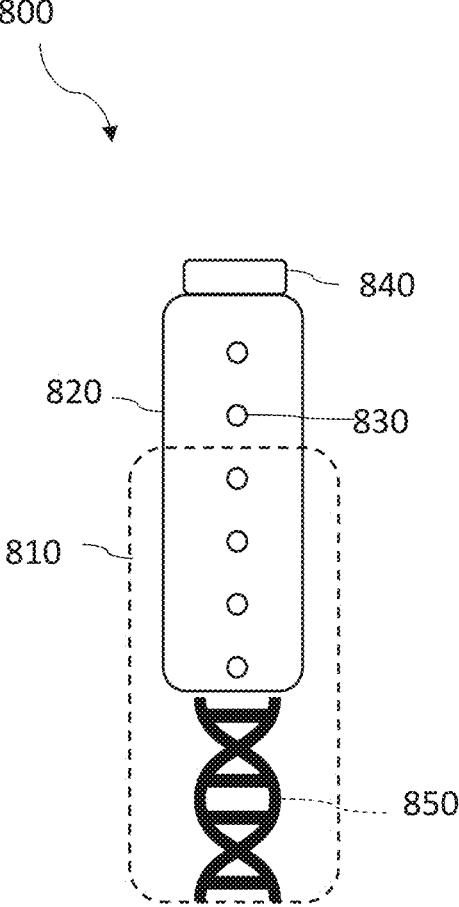
FIG. 8 depicts the use of a micro-actuator to push the internal telescoping tube away from the outer telescoping tube, according to an exemplary embodiment of the present invention.
Figure 9:
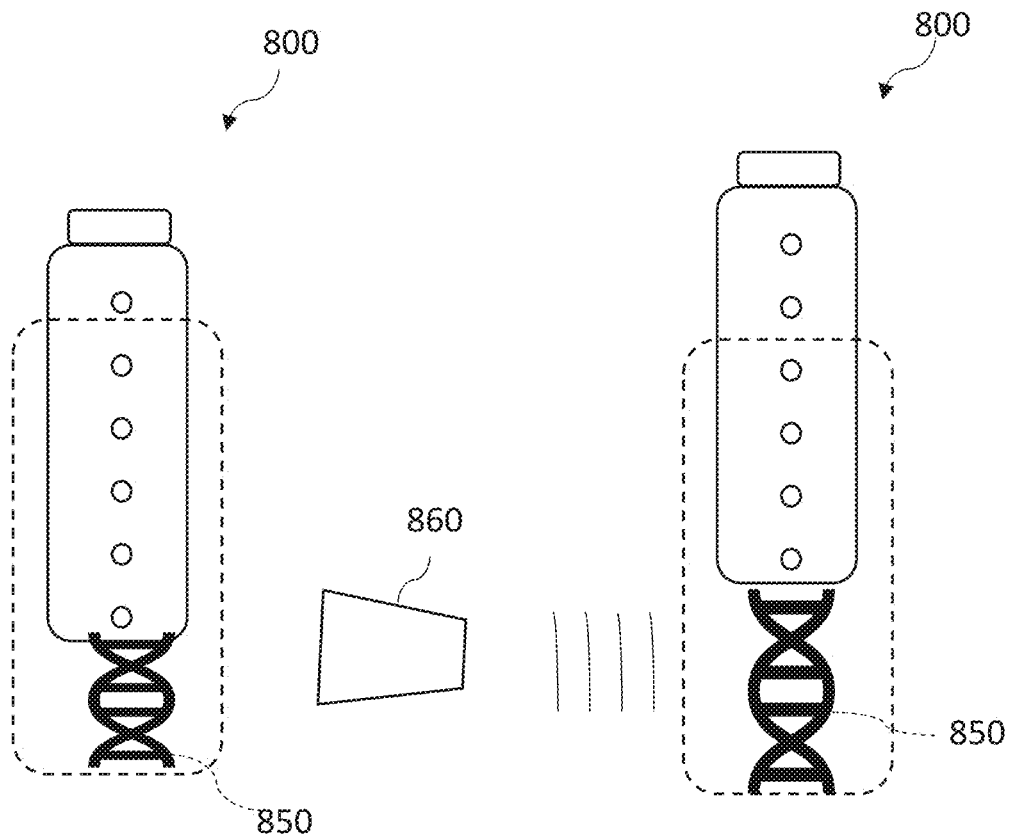
FIG. 9 depicts an increase in the length of the micro-actuator using an external controller and applicator of energy, according to an exemplary embodiment of the present invention.

Referring to FIG. 8 which shows an interbody spinal cage 800 that has telescoping outer tube 810 and inner tube 820, holes 830 in the outer tube for the retention pins, and a pressure sensor 840. FIG. 8 also shows an actuator 850 for moving the inner tube 820 relative to outer tube 810. The actuator 850 can provide for active actuation of the telescoping tubes. Unlike the springs that keep the inner tube in an extended state, the actuator 850 can push or pull the inner tube. FIG. 9 is a schematic diagram showing the operation of the actuator 850 by a controller 860. The controller 860 can be external to the body in which the disclosed interbody spinal cage is planted. The controller 860 can be operated to push or pull the inner tube, wherein the actuator 850 can be operated non-invasively by the external controller. FIG. 9 shows the expansion of the actuator 850 resulting in pushing of the inner tube causing an increase in height of the variable length rod. To adapt the contour of the interbody spinal cage to adjacent bones, first, the optimum lengths for each of the variable-length rods can be determined, for example using imaging techniques. Thereafter, the locking pins of the variable length rods can be disengaged. Once the locking pins have been disengaged, the lengths of variable length rods can be adjusted to optimum lengths by operating the actuator using the external controller. After achieving the optimum lengths, the corresponding locking pins can be re-engaged and the external controller can be removed. Alternatively, all the locking pins can be first disengaged. Thereafter, the positions of the two adjacent bones can be manipulated to the desired orientations by external manipulation of body postures, such as stretching of the body under medical instruction and supervision. The external controller can then activate actuators so that the interbody cage is deformed by elongation and contraction of respective variable length rods, depending on the desired outcome/effect. Readings from the pressure sensors can be taken to determine the pressure between the variable length rods and the bone, and accordingly, the controller can selectively operate the multiple variable lengths rods for their optimum lengths. While the embodiments have been described using locking pins, it is to be noted that the actuator can have a mechanism to restrict the movement of the telescoping tubes relative to each other, thus the locking pins may not be needed, and such actuators that can restrict the movement of the inner tube at desired length is within the scope of the present invention. Movement of the inner tube in both directions i.e., inside and outside of the outer tube can be restricted by the internal actuator.

Figures 10A, 10B, 10C:
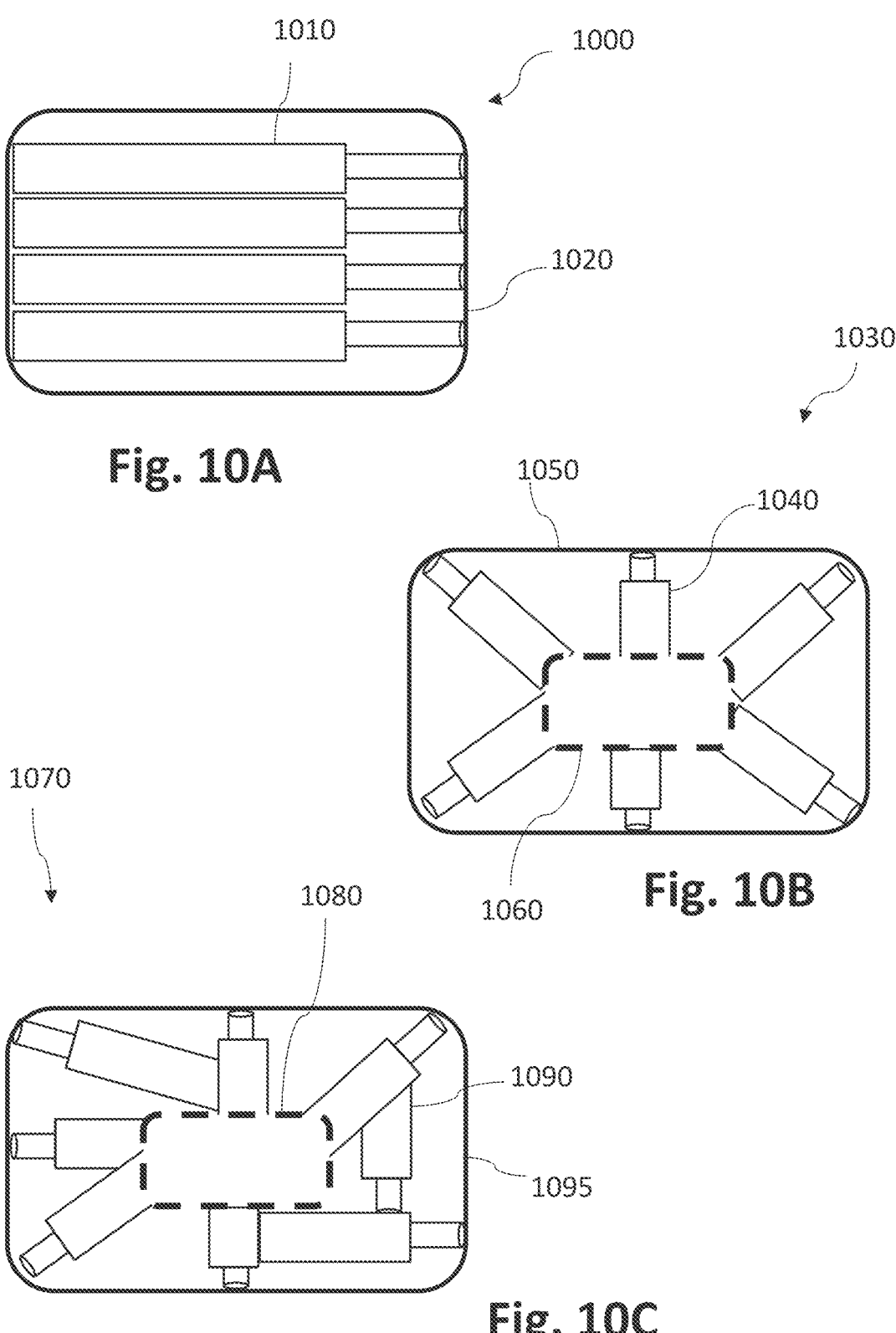
FIGS. 10A-10C show various arrangements of the vari-able-length rod of the disclosed interbody spinal cage.

Referring to FIGS. 10A, 10B, and 10C which show different arrangements of the variable-length rods within the flexible shell. FIG. 10A shows the interbody cage 1000 having multiple variable-length rods 1010 arranged horizontally within a flexible shell 1020, wherein all the variable-length rods are substantially parallel to each other and aligned horizontally. In another implementation, FIG. 10B shows the interbody cage 1030 has variable-length rods 1040 radially arranged, like vertices of a star shape within a flexible shell 1050 and mounted to an anchor 1060. Still in another implementation, shown in FIG. 10C is an interbody spinal cage 1070 having the variable-length rods 1090 arranged randomly within the flexible shell 1095 and the variable-length rods 1090 mounted to an anchor 1080. While FIGS. 10A-10C show a two-dimensional cross-sectional view, a person reading this disclosure will understand that the rods can be distributed spatially in three dimensions.

Figure 11:
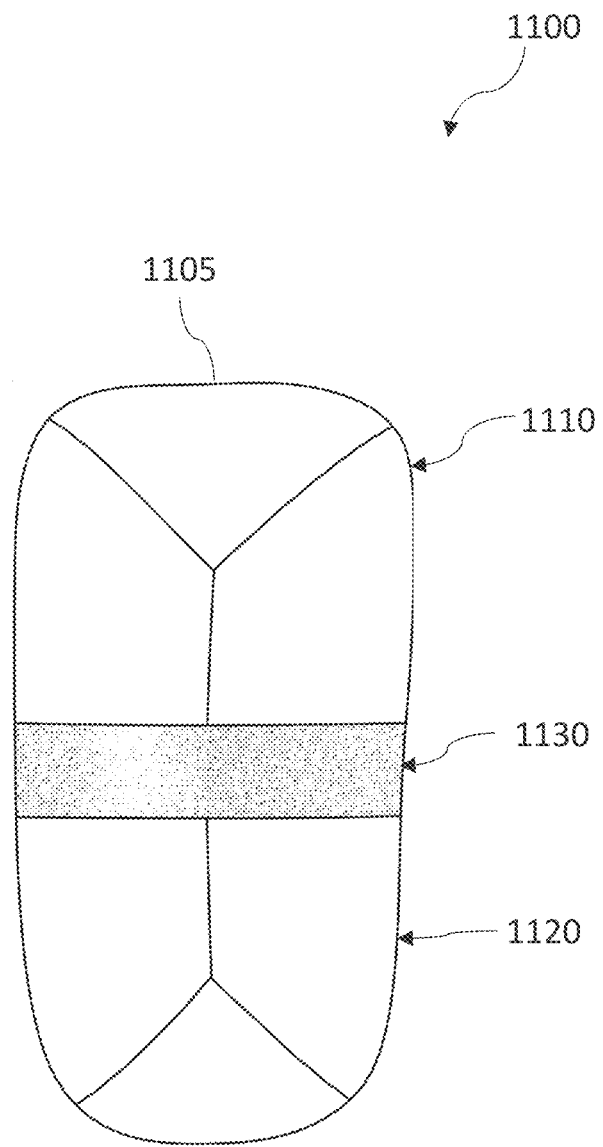
FIG. 11 shows a rod enclosed in an extensible hermetic joint to support the element of the interbody spinal cage, according to an exemplary embodiment of the present invention.

In certain implementations, the disclosed interbody spinal cage can be made from several support elements, wherein each of the several support elements can include one or more variable-length rods as described above. Referring to FIG. 11, which shows a support element 1100 of the disclosed interbody spinal cage. The support element includes a shell that encases one or more of the variable-length rods, wherein lengths of one or more variable-length rods can be adjusted. By changing the lengths of one or more of the variable-length rods, the overall length of the support element can be modified. As shown in FIG. 11, the shell 1105 of the support element can include an upper part 1110, a lower part 1120, and a middle part 1130, the middle part extends between the upper part and the lower part. The upper part and the lower part can be made from a rigid and biocompatible material, such as Titanium. The middle part can be made of extensible material that may also be biocompatible. The middle part can be hermetically sealed to the upper part and the lower part to prevent any ingress of fluid.

Figure 12:
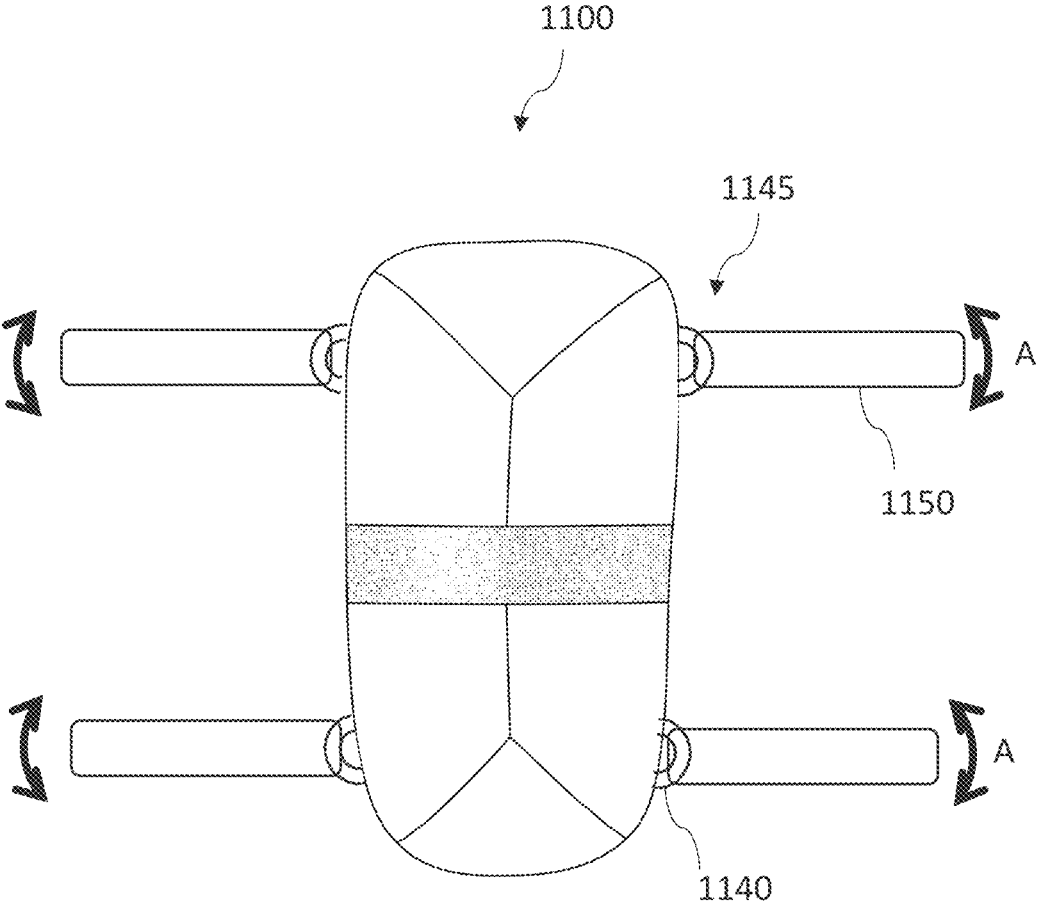
FIG. 12 shows a rod enclosed in an extensible hermetic joint to support the interbody spinal cage and connection through hinges and lateral bars connected to the support element, according to an exemplary embodiment of the present invention.
Figure 13:
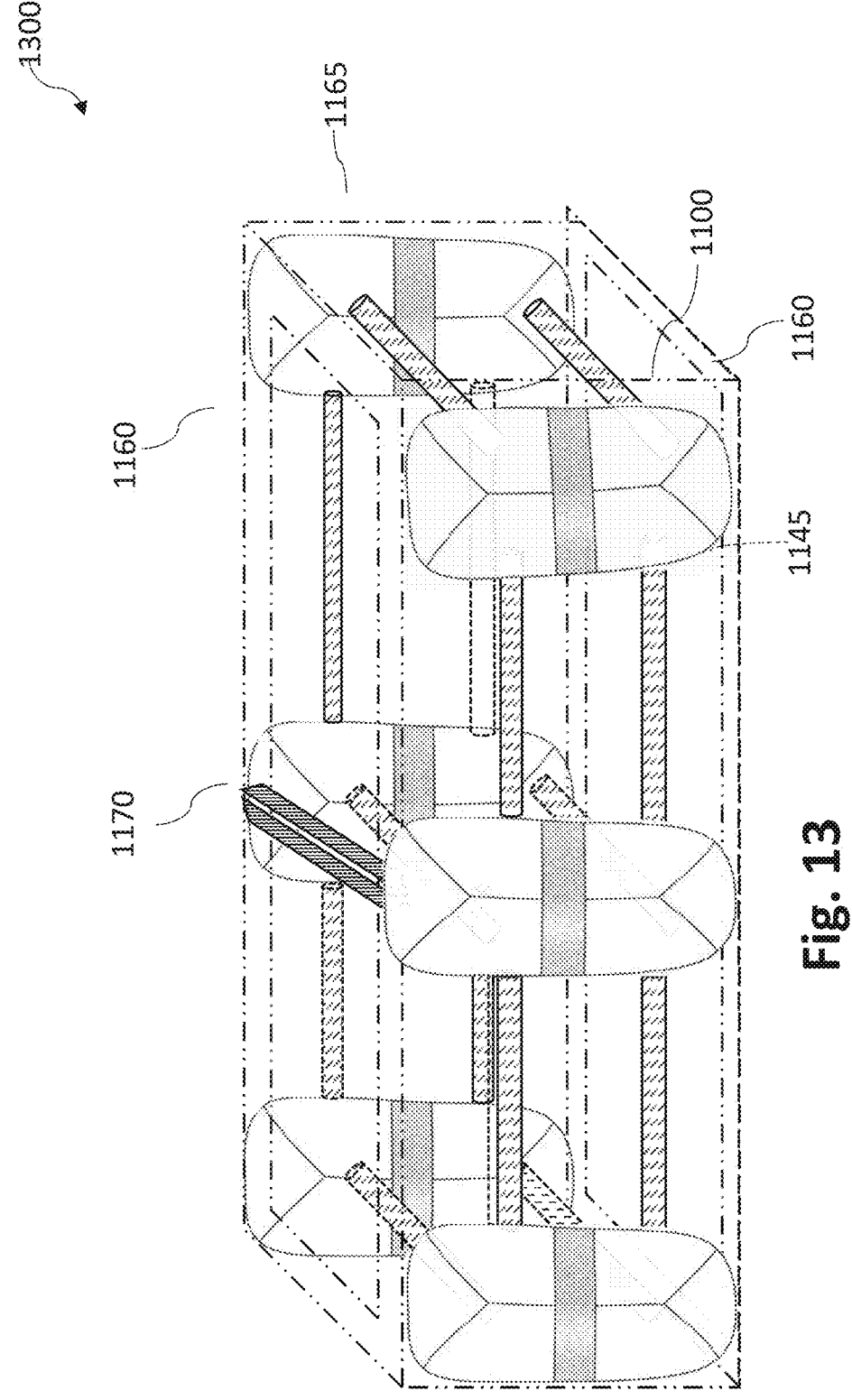
FIG. 13 shows a rectangular-shaped interbody spinal cage, according to an exemplary embodiment of the present invention.

Several support elements can be assembled into the disclosed interbody cage using linking members in a predetermined pattern, geometry, or arrangement to form the disclosed interbody spinal cage. Referring to FIG. 12 which shows the support element 1100 and linking members 1145 attached to the support element. The linking member 1145 can include a lateral bar 1150 and a hinge 1140, wherein the hinge permits the lateral bar to pivot in a direction shown by arrows "A" in FIG. 12. Referring to FIG. 13 which shows an exemplary embodiment of the disclosed interbody spinal cage 1300. The interbody spinal cage can be rectangular and include six support elements 1100 arranged in three parallel rows. The support elements 1100 are coupled with the linking members 1145. The joint 1170 in the middle section allows for a joint to be formed in the profile. The disclosed interbody spinal cage 1300 can include a frame having a rigid top and rigid bottom 1160, and an extensible wall 1165 that extends between the rigid top and rigid bottom. The frame can also have a joint 1170 that can divide the frame into two sections, wherein the two sections of the frame can flex towards each other at the joint, so that it may better conform to the shape of the bone. All components of the disclosed interbody spinal cage 1300 can be made of biocompatible material.

Figure 14:
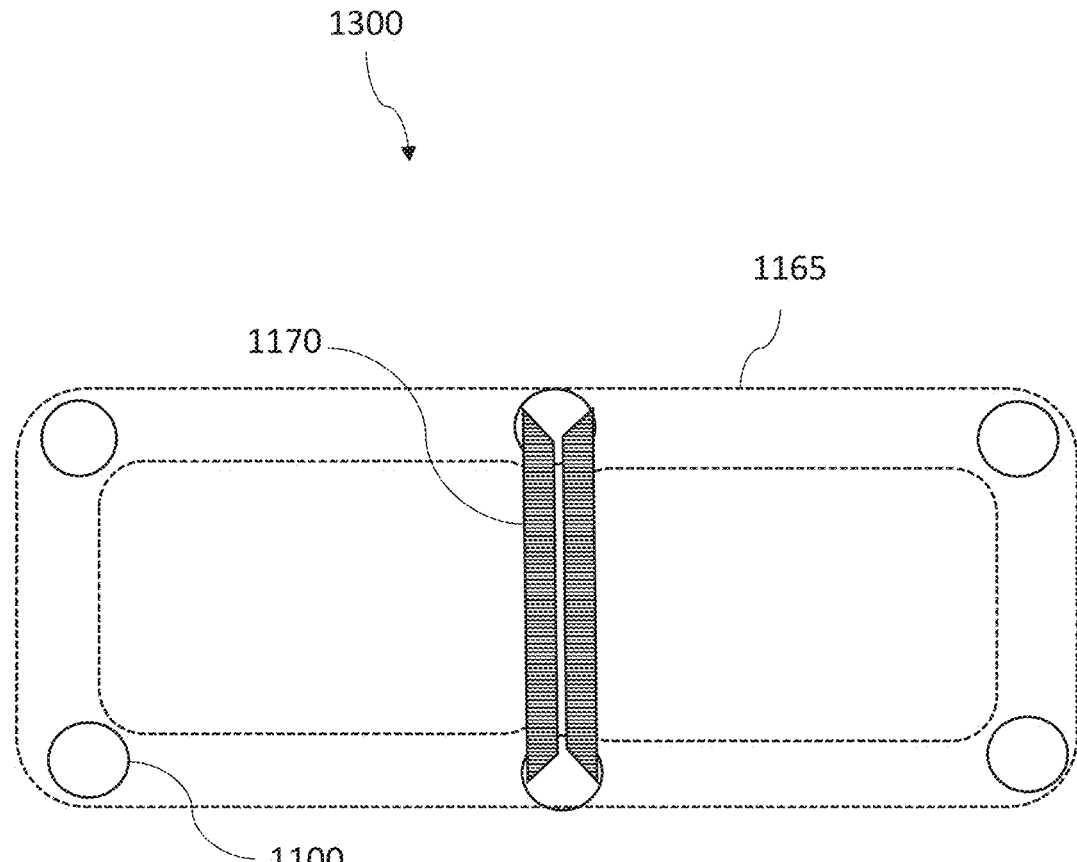
FIG. 14 is a top view of an interbody spinal cage having a 2×3 arrangement of support elements and a single joint, according to an exemplary embodiment of the present invention.
Figure 15:
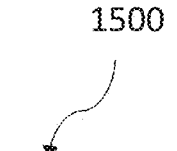
FIG. 15 is a top view of an interbody spinal cage having a 3×(5+2+5) arrangement of support elements and a single joint, according to an exemplary embodiment of the present invention.
Figure 15:
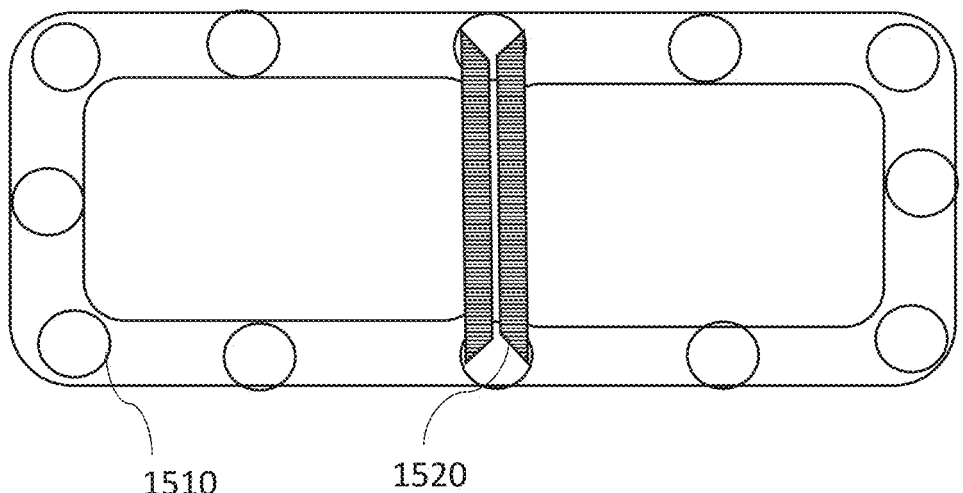

Referring to FIG. 15 which shows another embodiment of a rectangular interbody spinal cage 1500 formed of multiple support elements 1510, having more support elements compared to FIG. 14. A single joint 1520 in the middle section allows desired flex.

Figure 16:
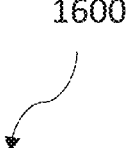
FIG. 16 is a top view of an interbody spinal cage showing an arrangement of support elements and a single joint, according to an exemplary embodiment of the present invention.
Figure 16:
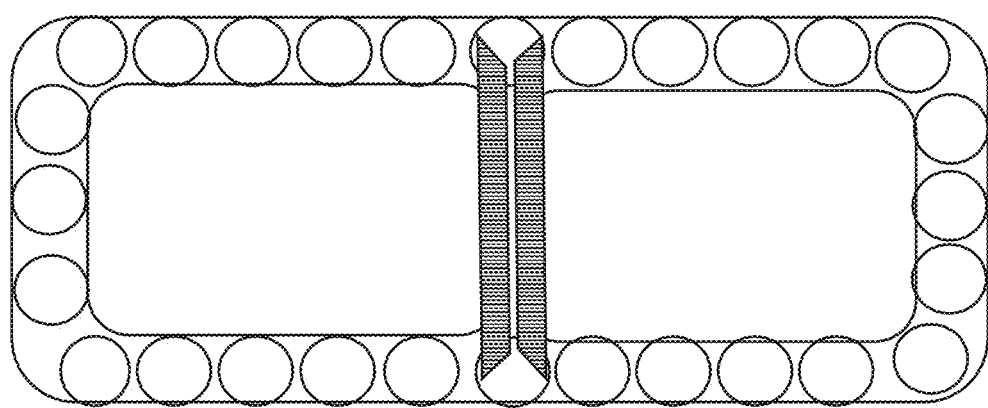
Figure 17:
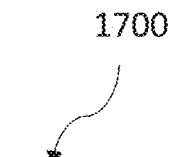
FIG. 17 is a top view of a smaller and rectangular interbody spinal cage showing an arrangement of support elements without any joint, according to an exemplary embodiment of the present invention.
Figure 17:
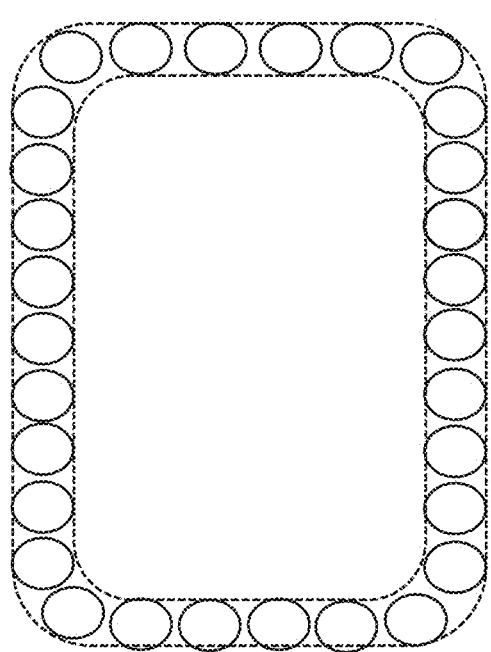
Figure 18:
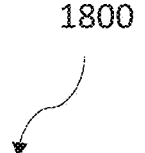
FIG. 18 depicts the top view of a cage embodiment in the form of a rectangular shape with multiple joints.
Figure 18:
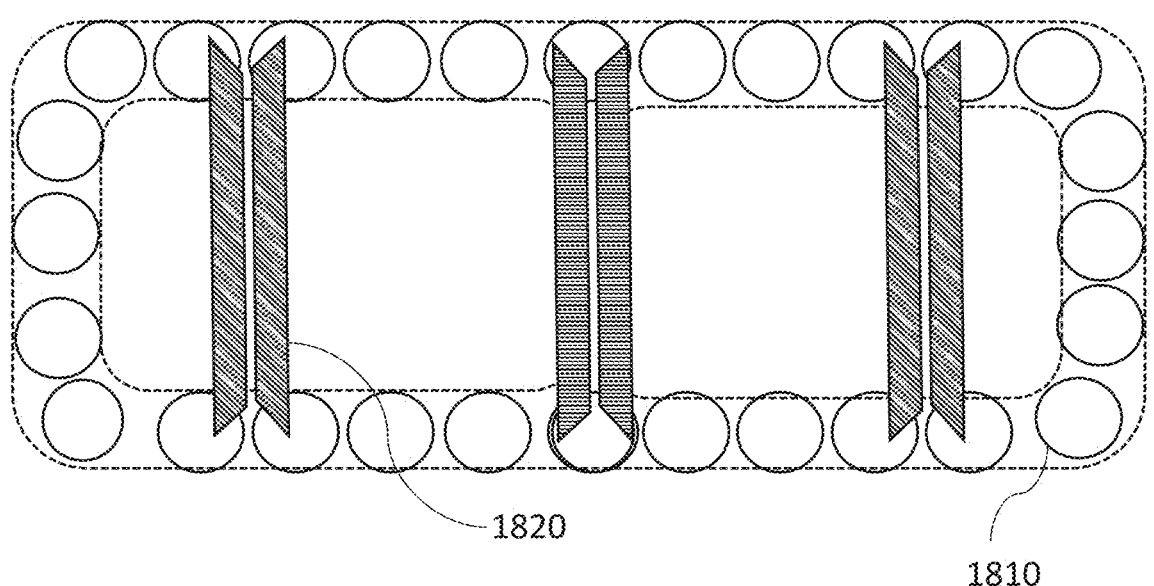
Figures 19A, 19B, 19C:
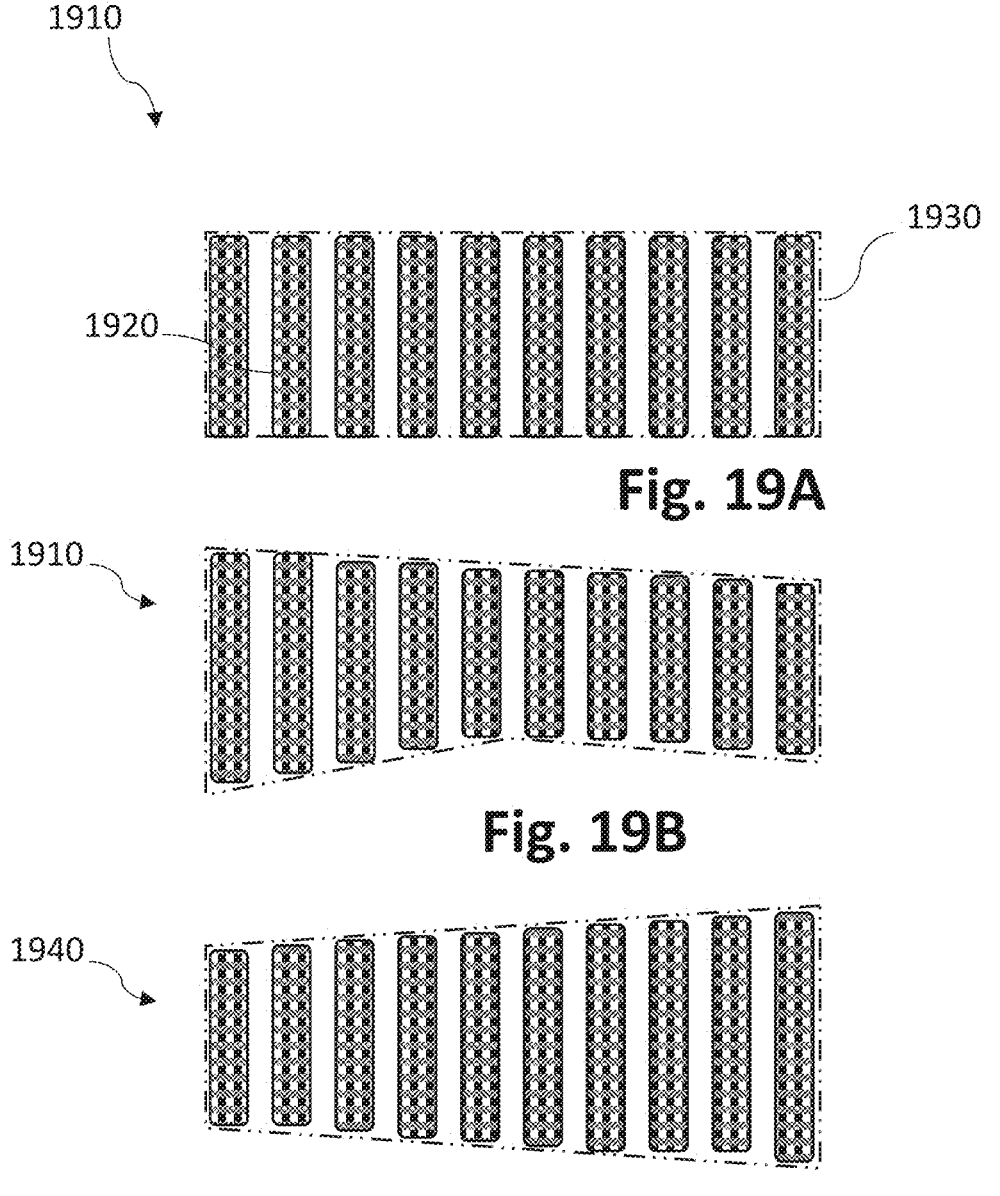
FIG. 19A is a lateral view of a rectangular interbody spinal cage without any adjustments in the variable-length rods, according to an exemplary embodiment of the present invention.
FIG. 19B shows the interbody spinal cage of FIG. 19A but with readjustments in the variable-length rods, according to an exemplary embodiment of the present invention.
FIG. 19C shows the interbody spinal cage of FIG. 19A but with readjustments in the variable-length rods, according to an exemplary embodiment of the present invention.

Referring to FIG. 16 depicts another embodiment of a rectangular interbody spinal cage 1600 that can include more of the support elements. This configuration may allow for more mechanical support for the top and bottom perimeters. Therefore, the load-bearing capacity can be increased. The joint in the middle section allows for a joint to be formed in the profile. Referring to FIG. 17 which shows an embodiment of a small rectangular interbody spinal cage 1700 without any joint (top view). The number of support elements is in such a way that they form a continuous line. This configuration allows for more load-bearing mechanical support for the top and bottom perimeters. FIG. 18 depicts another embodiment of a rectangular interbody spinal cage 1800 formed of multiple joints 1820 and support elements 11810 (top view) in such a way that support elements form a continuous line. This configuration allows for more support for the top and bottom perimeters. The multiple joints in the left, middle and right sections allow for joints to be formed in the profile, creating more adaptability with the bone profile. All components are made of biocompatible material. FIG. 19A-C depicts possible profiles that can be obtained with the interbody spinal cage (lateral view). FIG. 19A shows a rectangular shape interbody spinal cage 1910 having a series of support elements 1920 encased in a frame, that includes an inner and outer extensible mesh, and rigid top and bottom, however, it is understood that any or both of the top and bottom of the frame can be semi-rigid without departing from the scope the present invention. FIG. 19B shows the interbody spinal cage 1910 as in FIG. 19A but deformed due to change in lengths of the support elements and flex at a middle joint. FIG. 19C shows the deformed interbody spinal cage 1940 that does not have a joint.

Figures 20A, 20B, 20C:
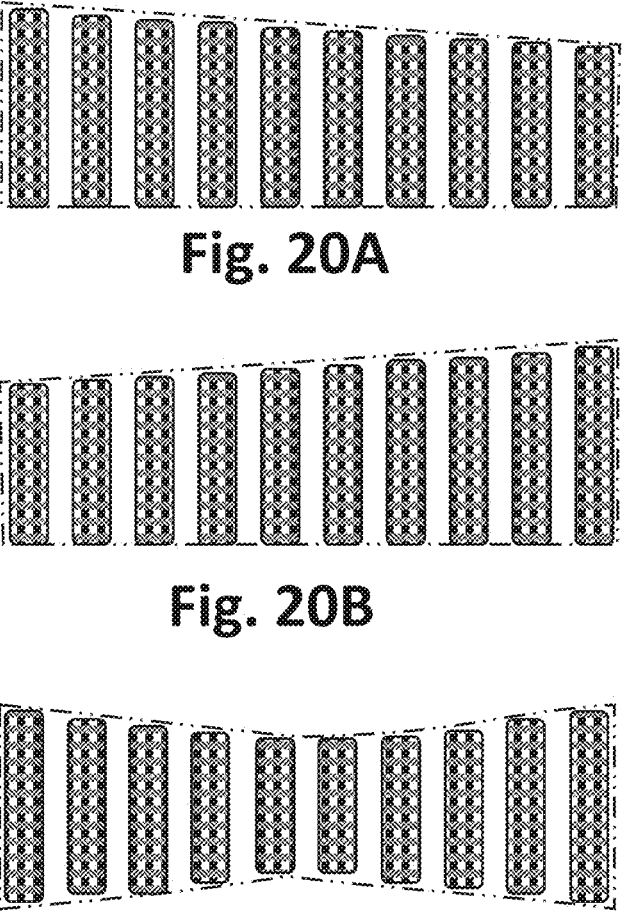
FIG. 20A is a lateral view of the interbody spinal cage showing a different profile obtained by adjusting the dimensions of the support element, according to an exemplary embodiment of the present invention.
FIG. 20B is a lateral view of the interbody spinal cage showing a different profile obtained by adjusting the dimensions of the support elements, according to an exemplary embodiment of the present invention.
FIG. 20C is a lateral view of the interbody spinal cage showing a different profile obtained by adjusting the dimensions of the support elements, according to an exemplary embodiment of the present invention.

FIG. 20A-C depicts some more possible profiles that can be obtained with the change in dimensions of the disclosed interbody spinal cage (lateral view). FIGS. 20A and 20B show two possible profiles obtained from a rectangular interbody spinal cage, while FIG. 20C shows a profile obtained by flex at the joint.

Figure 21:
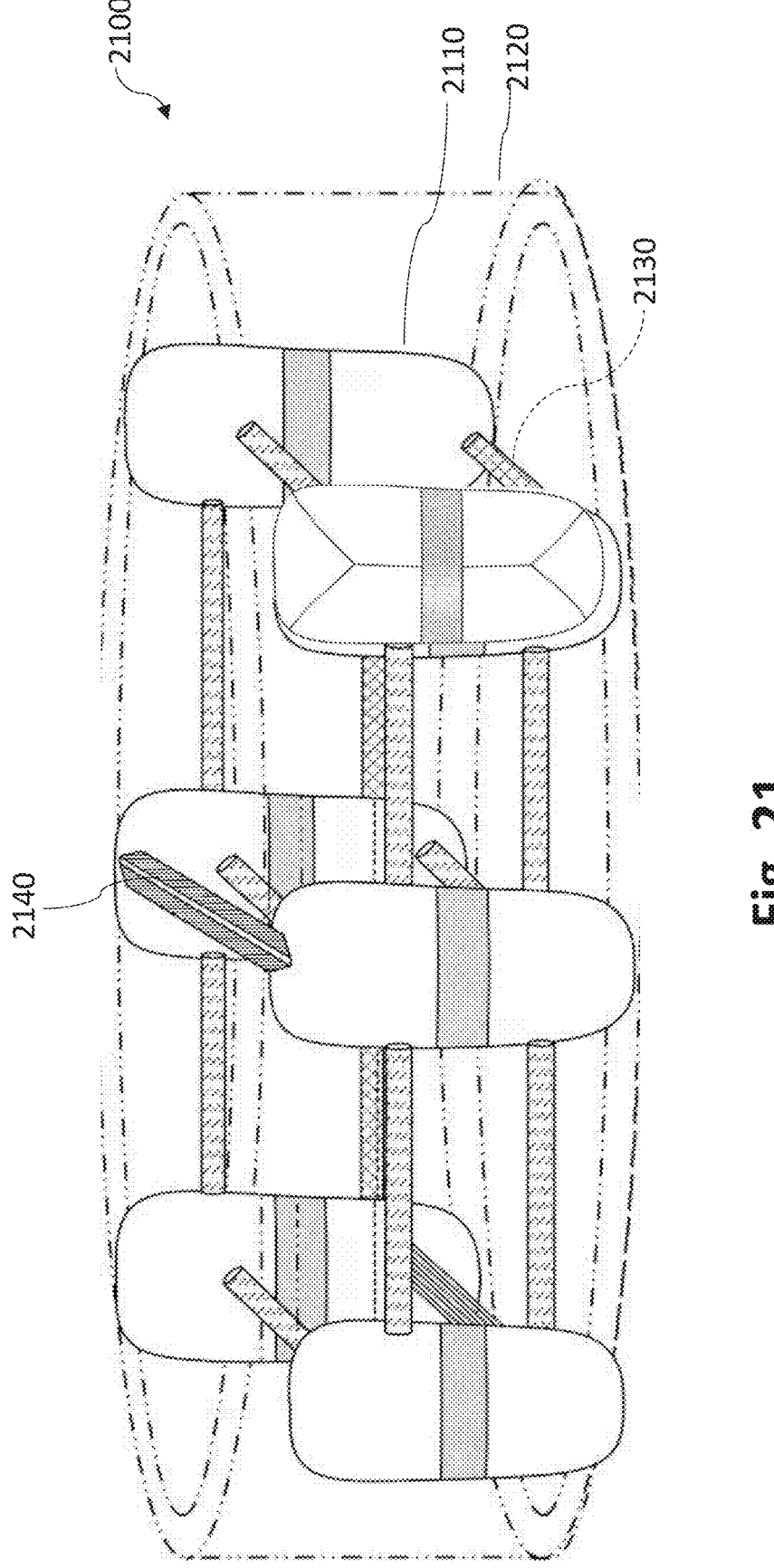
FIG. 21 is a front perspective view of an ellipsoid-shaped interbody spinal cage that has 2×3 support elements and a single joint, according to an exemplary embodiment of the present invention.
Figure 22:
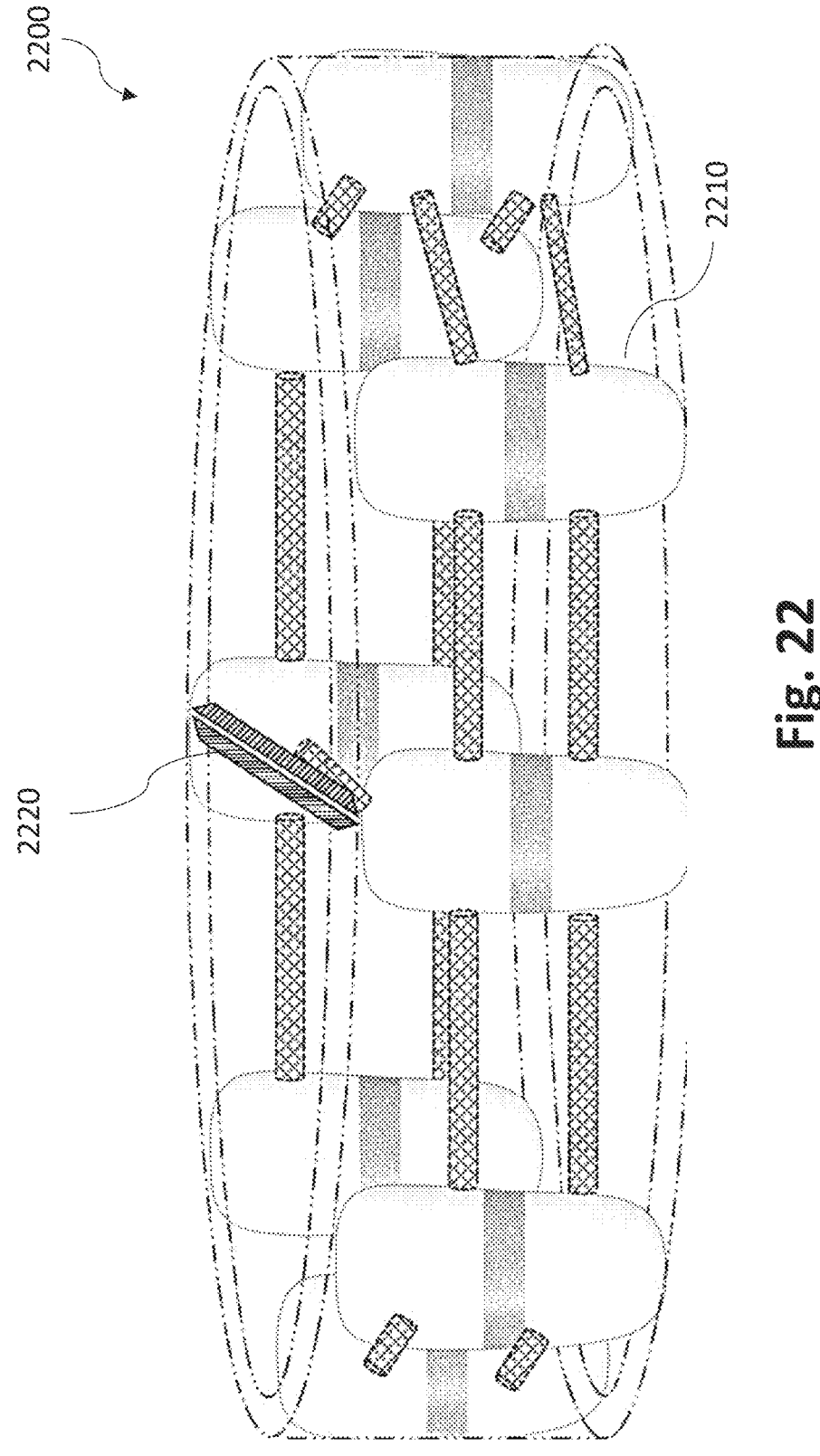
FIG. 22 is a front perspective view of an ellipsoid interbody spinal cage that has a (3+2+3) arrangement of the support elements and a single joint, according to an exemplary embodiment of the present invention.

FIG. 21 depicts another embodiment of an interbody spinal cage 2100 of an ellipsoidal shape, having six support elements 2110, a single joint 2140, encased in a frame 2120, and linking members 2130 coupling the six support elements. The number of support elements can be varied without departing from the scope of the present invention. For example, FIG. 22 shows the same interbody spinal case as in FIG. 21, however, the interbody spinal cage 2200 has eight support elements 2210 while a single joint 2220.

Figure 23:
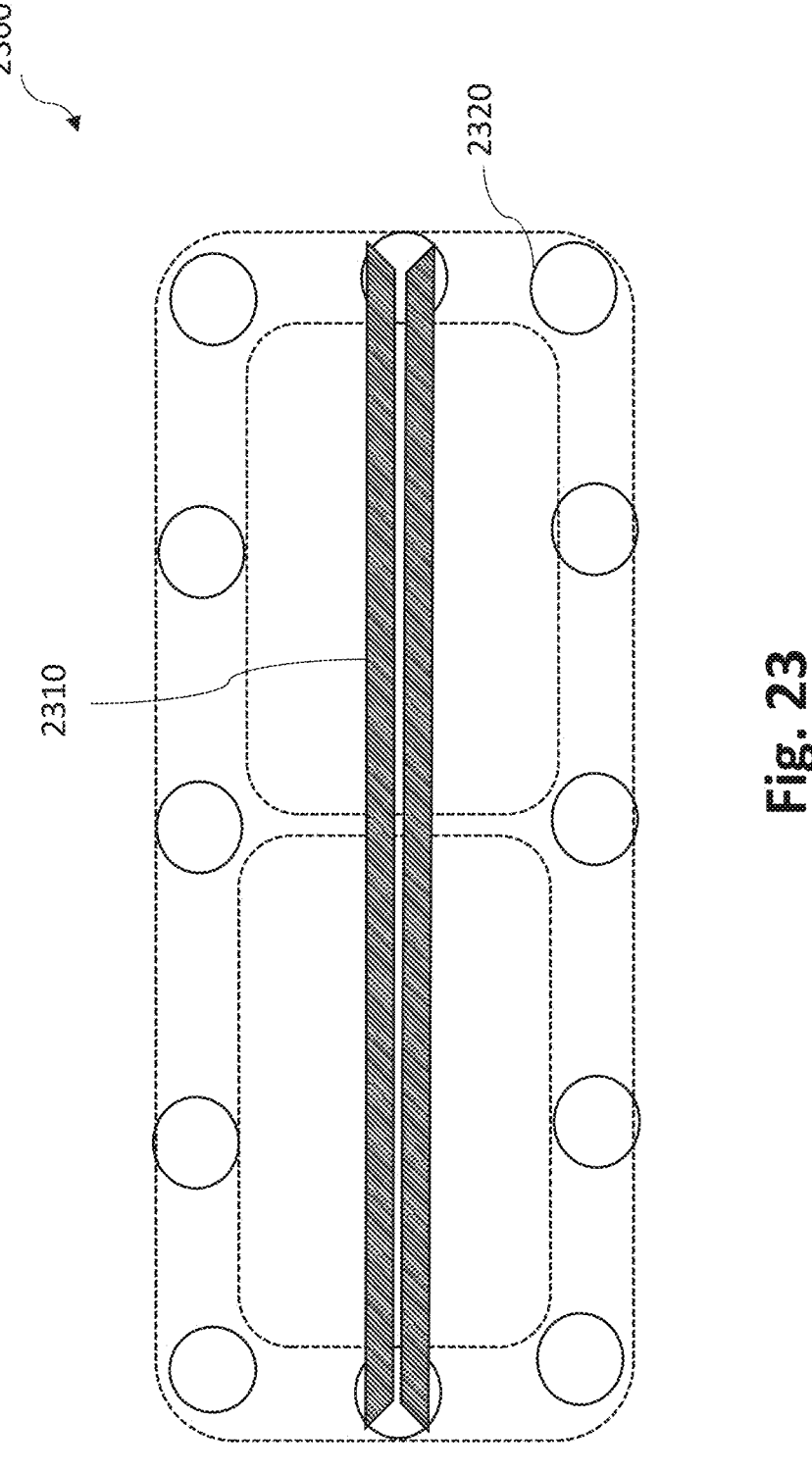
FIG. 23 is a top view of a rectangular interbody spinal cage that has a (5+2+5) arrangement of the support elements and a traversal single joint, according to an exemplary embodiment of the present invention.
Figure 24:
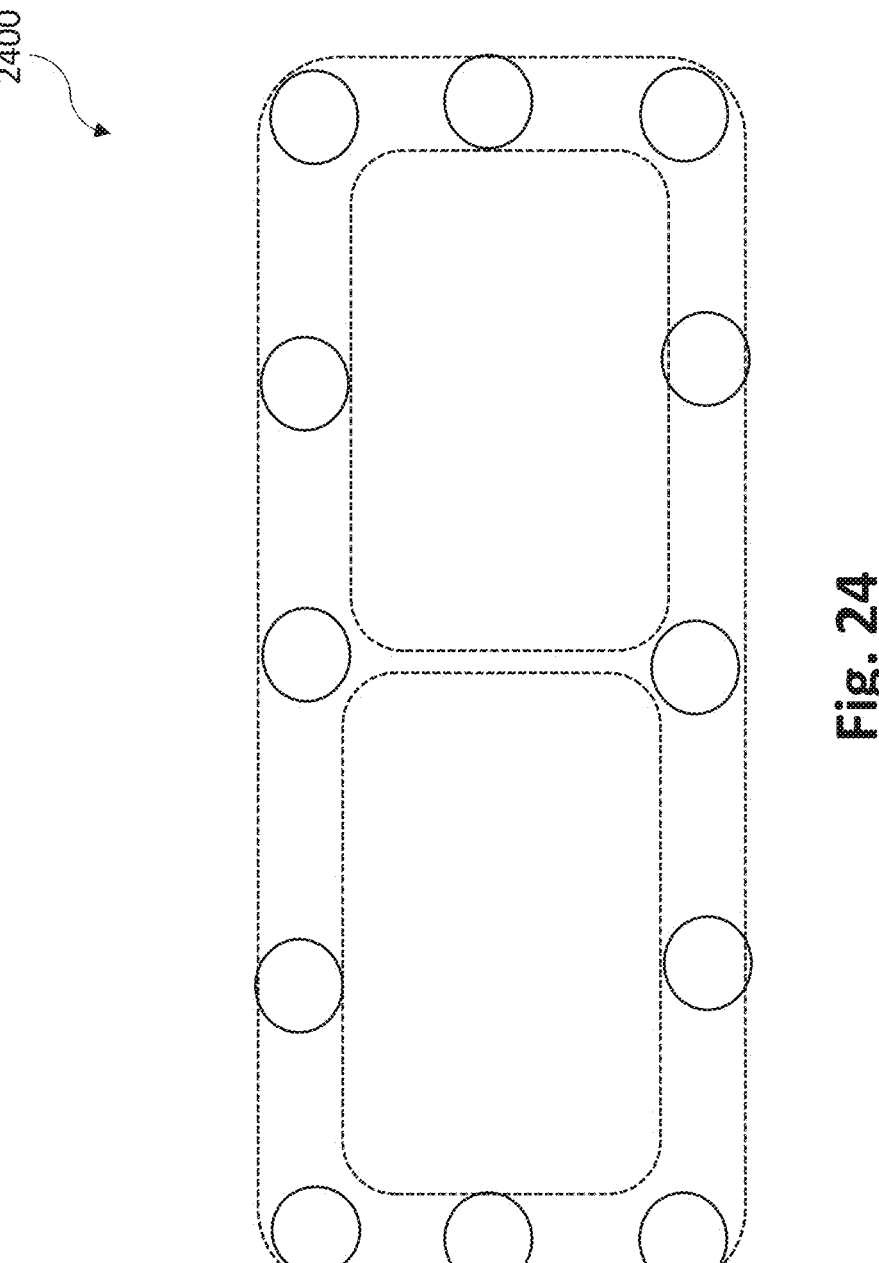
FIG. 24 is a top view of a rectangular interbody spinal cage that has a (5+2+5) arrangement of the support elements and no joint, according to an exemplary embodiment of the present invention.

Referring to FIG. 23 depicts another embodiment of a rectangular interbody spinal cage 2300 formed of multiple support elements 2320 and a joint 2310 that extends laterally (from left to right) and allows for flexion in the frame obtaining a different profile. FIG. 24 shows similar rectangular interbody spinal cage 2400 but without a joint.

Figure 25:
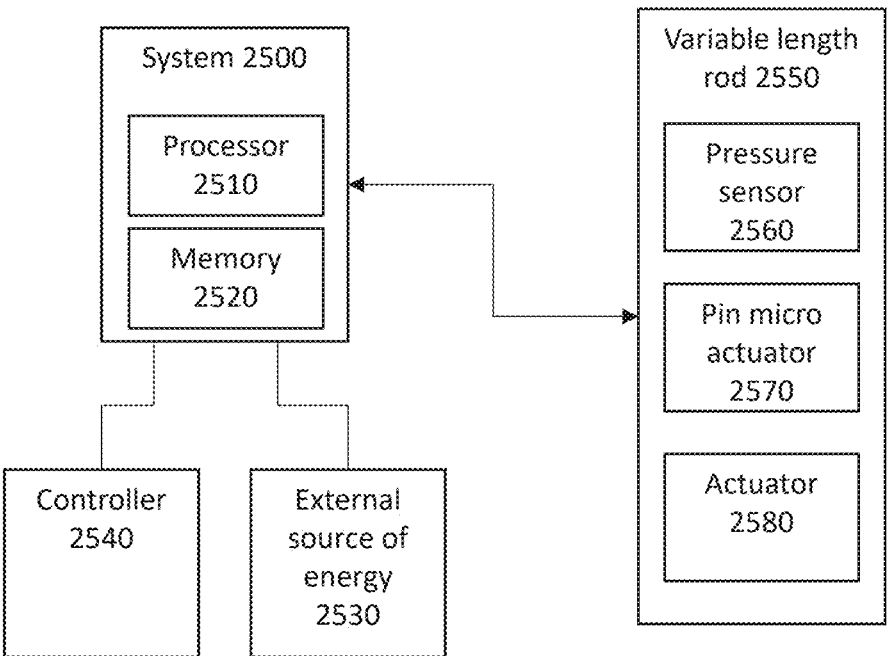
FIG. 25 illustrates the disclosed system operating on a variable-length rod by an external controller, according to an exemplary embodiment of the present invention.

FIG. 25 depicts a disclosed assembly including a system 2500 that can include a processor 2510 and a memory 2520. The system may be connected to a display and can include a visualization system. The assembly can further include a controller 2540 for operating actuator 2580 of a variable-length rod 2550, the actuator 2580 can move the inner tube of the variable-length rod 2550. Also, the assembly can include an external source of energy 2530 for operating the pin micro actuator 2570. The disclosed system 2500 can receive pressure reading values from a pressure sensor 2560 of the variable-length rod 2550. The sensed data are mapped by the system 2500 so that the medical expert can decide about the length of each of the variable length rods in each one the support elements. The mapping may use heat maps to conveniently display the pressure values. The system can include an optimization software comprising machine learning algorithms that can assist the medical expert in deciding about the optimal lengths of the supports.

While particular embodiments have been described, it should be appreciated that the embodiments should not be construed as limited by such description, but rather construed according to the claims.

What is claimed is:

1. An interbody spinal cage comprising: a plurality of support elements, wherein each of the plurality of support elements comprises a shell encasing one or more variable length rods, each of the one or more variable length rods comprises: an inner tube that has a proximal end and a distal end, an outer tube that has a proximal end and a distal end, wherein the distal end of the inner tube is slidably received within the outer tube through the proximal end of the outer tube, wherein the inner tube is configured to telescopically slide within the outer tube, a retention member configured to limit movement of the inner tube relative to the outer tube, a retention member micro-actuator configured to selectively engage and disengage the retention member, and a tube actuator coupled to the distal end of the inner tube and configured to at least push the inner tube relative to the outer tube, wherein the shell is extensible in at least one direction, wherein extension of each shell is caused by the one or more variable length rods; and a plurality of linking members configured to assemble the plurality of support elements into a frame.

2. The interbody spinal cage according to claim 1, wherein the shell comprises an upper rigid section, a lower rigid section, and a middle extensible section, wherein the middle extensible section extends between the upper rigid section and the lower rigid section.

3. The interbody spinal cage according to claim 1, wherein the frame comprises a rigid top, a rigid bottom, and an extensible mesh wall that perpendicularly extends between the rigid top and the rigid bottom.

4. The interbody spinal cage according to claim 3, wherein the frame further comprises a joint configured to divide the frame into two sections, wherein the two sections are capable of being flexed at the joint.

5. The interbody spinal cage according to claim 1, wherein each of the one or more variable length rods comprises a pressure sensor configured to measure a force on the inner tube.

* * * * *